(12) United States Patent
Cheatham, III et al.

(10) Patent No.: US 9,707,407 B2
(45) Date of Patent: *Jul. 18, 2017

(54) ELECTROSHOCK DEVICE FOR MONITORING TARGET RESPONSE

(71) Applicant: Elwha LLC, Bellevue, WA (US)

(72) Inventors: Jesse R. Cheatham, III, Seattle, WA (US); Hon Wah Chin, Palo Alto, CA (US); Alexander G. Hyde, Redmond, WA (US); Roderick A. Hyde, Redmond, WA (US); Jordin T. Kare, San Jose, CA (US)

(73) Assignee: Elwha LLC, Bellevue, WA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/172,669

(22) Filed: Jun. 3, 2016

(65) Prior Publication Data

US 2016/0279433 A1 Sep. 29, 2016

Related U.S. Application Data

(63) Continuation of application No. 14/097,038, filed on Dec. 4, 2013, now Pat. No. 9,381,372.

(51) Int. Cl.
*A61N 1/00* (2006.01)
*A61N 1/39* (2006.01)
(Continued)

(52) U.S. Cl.
CPC ........... *A61N 1/3987* (2013.01); *A61N 1/046* (2013.01); *A61N 1/3925* (2013.01); *A61N 1/3968* (2013.01); *F41H 13/0025* (2013.01)

(58) Field of Classification Search
CPC .... A61N 1/3987; A61N 1/046; A61N 1/3925; A61N 1/3968; F41H 13/0025
(Continued)

(56) References Cited

U.S. PATENT DOCUMENTS 4,884,809 A   12/1989   Rowan
5,698,815 A   12/1997   Ragner
(Continued)

FOREIGN PATENT DOCUMENTS

AR    WO 2013053033 A1 *   4/2013   ......... F41H 13/0025
WO    WO 2013/053033       4/2013

OTHER PUBLICATIONS

Machine Translation of WO2013/053033A1 from WIPO Patentscope using Google Translate, Downloaded Aug. 20, 2015.*
(Continued)

*Primary Examiner* — Michael Carey
(74) *Attorney, Agent, or Firm* — Foley & Lardner LLP

(57) ABSTRACT

An electroshock device for delivering an electrical discharge to a target includes an electrical discharge circuit, and an electrode coupled to the electrical discharge circuit and having an attachment feature attachable to the target. Upon attachment the electrode is enabled to monitor a physiological condition of the target, generate a signal based on the physiological condition, and deliver the electrical discharge to the target. The electroshock device also includes a controller communicatively coupled to the electrical discharge circuit and the electrode. The controller is configured to modulate delivery of the electrical discharge based on the physiological condition of the target.

34 Claims, 8 Drawing Sheets

(51) Int. Cl.
*A61N 1/04* (2006.01)
*F41H 13/00* (2006.01)

(58) Field of Classification Search
USPC .................................. 607/6, 7, 115, 145, 1, 2
See application file for complete search history.

(56) References Cited

U.S. PATENT DOCUMENTS

| | | | |
|---|---|---|---|
| 6,898,887 B1 | 5/2005 | Stratbucker | |
| 7,057,872 B2 | 6/2006 | Smith et al. | |
| 7,221,552 B1 | 5/2007 | Brown | |
| 7,280,340 B2 | 10/2007 | Smith et al. | |
| 7,305,787 B1 * | 12/2007 | Stratbucker | F41H 13/0025 42/1.08 |
| 7,602,597 B2 | 10/2009 | Smith et al. | |
| 7,701,692 B2 | 4/2010 | Smith et al. | |
| 7,886,648 B2 * | 2/2011 | Williams | F41H 13/0025 119/908 |
| 8,019,402 B1 | 9/2011 | Kryzpow et al. | |
| 8,087,335 B2 | 1/2012 | Shekarri | |
| 8,098,474 B2 | 1/2012 | Smith et al. | |
| 8,107,213 B2 | 1/2012 | Smith | |
| 8,154,844 B2 | 4/2012 | Brown | |
| 8,324,902 B2 | 12/2012 | Burns et al. | |
| 8,390,978 B1 | 3/2013 | Saliga | |
| 9,381,372 B2 * | 7/2016 | Cheatham, III | A61N 1/3987 |
| 2009/0219664 A1 | 9/2009 | Smith | |
| 2010/0069979 A1 | 3/2010 | Pittaro | |
| 2011/0013337 A1 | 1/2011 | Brown | |
| 2012/0202604 A1 | 8/2012 | Musial et al. | |
| 2012/0298119 A1 | 11/2012 | Reese et al. | |

OTHER PUBLICATIONS

Machine Translation of WO2013/053033 A1 from WIPO Patentscope using Google Translate. Downloaded Aug. 20, 2015.

* cited by examiner

ELECTROSHOCK DEVICE FOR MONITORING TARGET RESPONSE

CROSS-REFERENCE TO RELATED PATENT APPLICATIONS

The present application is a continuation of U.S. application Ser. No. 14/097,038, filed Dec. 4, 2013, now U.S. Pat. No. 9,381,372, which is incorporated herein by reference in its entirety.

BACKGROUND

Electroshock devices, or "stun guns," deliver a high-voltage, low-current electrical discharge for temporarily incapacitating a biological target. These devices may be used by police officers or other security personnel in order to restrain recalcitrant persons. Typically, the intensity (e.g., voltage) of the electrical discharge is predetermined or manually controlled by a user of the device. As a result, the electrical discharge may produce a non-desired outcome as delivered, depending on the physical characteristics (e.g., weight, heart rate, etc.) of the target and/or a delivery location on the target. For instance, a discharge having a relatively low intensity or short duration may not be sufficient to restrain a particular target, requiring an additional or longer discharge to temporarily incapacitate the target. On the other hand, a discharge having a relatively high intensity or long duration may have a negative impact on a particular target, such as triggering a cardiac condition in the target. Further, the cardiac condition may not include visible physical symptoms, such that the condition may not be immediately diagnosed and/or treated, or may be exacerbated by the continued electrical discharge.

SUMMARY

The foregoing summary is illustrative only and is not intended to be in any way limiting. In addition to the illustrative aspects, embodiments, and features described above, further aspects, embodiments, and features will become apparent by reference to the drawings and the following detailed description.

An embodiment of the present disclosure relates to an electroshock device for delivering an electrical discharge to a target. The electroshock device includes an electrical discharge circuit, an electrode coupled to the electrical discharge circuit and having an attachment feature attachable to the target. Upon attachment the electrode is enabled to monitor a physiological condition of the target, generate a signal based on the physiological condition, and deliver the electrical discharge to the target. The electroshock device also includes a controller communicatively coupled to the electrical discharge circuit and the electrode. The controller is configured to modulate delivery of the electrical discharge based on the signal.

Another embodiment of the present disclosure relates to an electroshock device for delivering an electrical discharge to a target. The electroshock device includes an electrical discharge circuit for providing the electrical discharge, a first electrode coupled to the electrical discharge circuit, a second electrode coupled to the electrical discharge circuit, and a controller coupled to the first and second electrodes and configured to receive one or more signals from the first and second electrodes and determine a position of the first and second electrodes based on the one or more signals. The first and second electrodes are attachable to the target and configured to deliver an electrical discharge from the electrical discharge circuit to the target.

Another embodiment of the present disclosure relates to an electroshock device. The electroshock device includes an electrical discharge circuit configured to provide an electrical discharge and a defibrillating pulse, and an electrode coupled to the electrical discharge circuit and being attachable to a target. The electroshock device includes an electroshock mode for delivering the electrical discharge and a defibrillating mode for delivering the defibrillating pulse. The electrode is configured to monitor a physiological condition of the target and generate a signal based on the physiological condition. The electroshock device also includes a controller coupled to the electrical discharge circuit and the electrode. The controller is configured to receive the signal from the electrode, modulate the electrical discharge and the defibrillating pulse based on the signal, and reconfigure the electroshock device between the electroshock mode and the defibrillating mode based on the signal.

Another embodiment of the present disclosure relates to a method for delivering an electrical discharge to a target. The method includes attaching an electrode to the target by projecting the electrode from an electroshock device, delivering the electrical discharge to the target via the electrode, monitoring a physiological condition of the target, and modulating the electrical discharge based on the physiological condition.

Another embodiment of the present disclosure relates to a method for delivering a defibrillating pulse to a target. The method includes delivering an electrical discharge to the target via an electrode projected from an electroshock device, monitoring a physiological condition of the target, determining whether the defibrillating pulse is required based on the physiological condition, and delivering the defibrillating pulse to the target based on a determination that the defibrillating pulse is required.

DETAILED DESCRIPTION

Figure 1A:
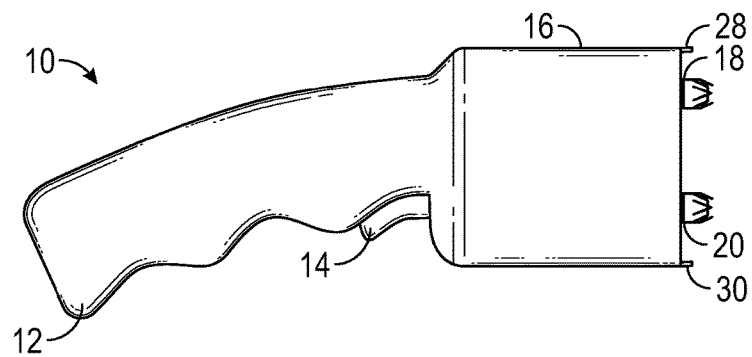
FIG. 1A is an illustration of an electroshock device, according to one embodiment.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Referring generally to the figures, an electroshock device is shown for delivering an electrical discharge (e.g., a relatively high voltage, low current electrical discharge) to a target (e.g., a biological target). In one embodiment, the electroshock device includes projectable electrodes for attaching to the target and delivering the electrical discharge. The electrodes are configured to monitor (i.e., sense) one or more physiological conditions of the biological target and generate one or more signals representing the one or more physiological conditions. The electroshock device includes a controller for receiving the one or more signals and modulating the electrical discharge based on the one or more physiological conditions of the target. For instance, if the physiological conditions comprise involuntary muscular conditions which indicate continued purposeful movement in the target, the controller may increase the intensity or duration of the electrical discharge in order to temporarily incapacitate the target. If the physiological conditions indicate that the target is incapacitated, or that the target may be harmed by a continued electric current, the controller may decrease the intensity or duration of the electrical discharge in order to prevent harm to the target. The electroshock device may also be configured to deliver a defibrillating pulse to the target when necessary. In one embodiment, the electrodes are configured to deliver the defibrillating pulse as well as the electrical discharge. The controller may determine when defibrillation is necessary, such as when the physiological conditions indicate an arrhythmia or fibrillation, causing the electrodes to deliver one or more defibrillating pulses to the target in order to prevent further harm to the target.

Figure 1B:
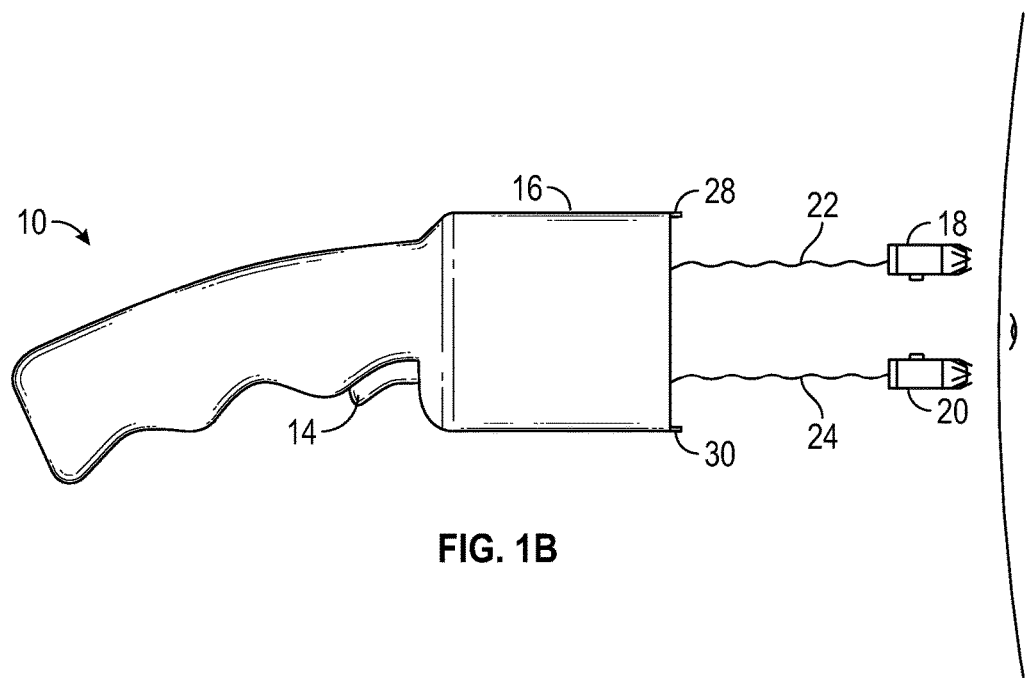
FIG. 1B is an illustration of the electroshock device when actuated, according to one embodiment.
Figure 1C:
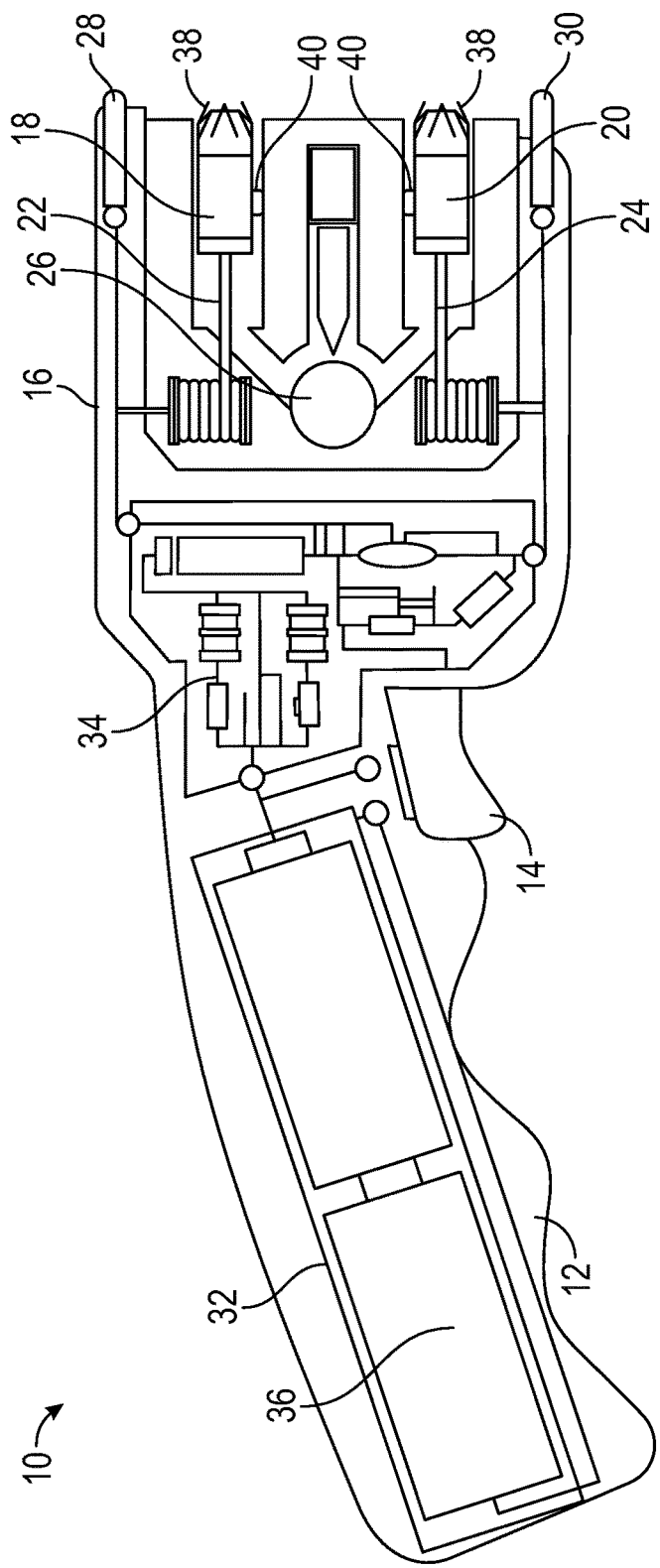
FIG. 1C is a schematic representation of the electroshock device, according to one embodiment.
Figure 2:
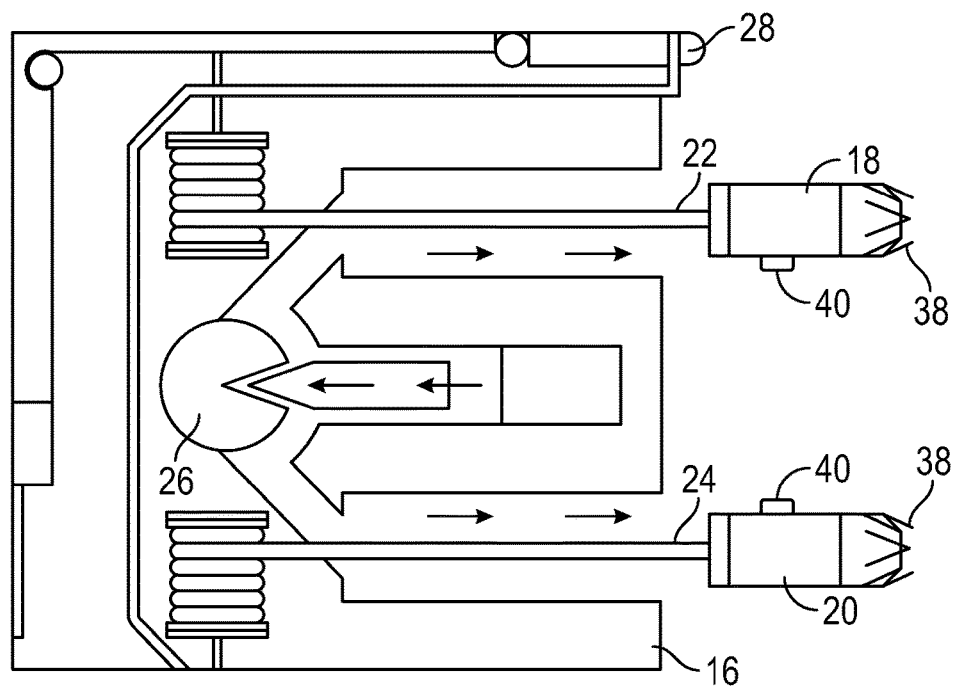
FIG. 2 is a close-up schematic representation of the electroshock device when actuated, according to one embodiment.

Referring to FIGS. 1 and 2, electroshock device 10 (e.g., taser device, defibrillating device, etc.) is shown, according to one embodiment. In this embodiment, device 10 is a handheld device including handle 12 connected to housing 16. Device 10 is shown in a non-actuated or resting configuration in FIG. 1A, but device 10 may be actuated (i.e., triggered) by pressing or pulling trigger 14 positioned on handle 12. When actuated (as shown in FIG. 1B), device 10 may be used to deliver an electrical discharge (e.g., an electric current) intended for a biological target (e.g., an attacker), such as to temporarily incapacitate the target.

Device 10 includes first electrode 18 (e.g., probe) and second electrode 20 (e.g., probe). In the non-actuated configuration of FIG. 1A, electrodes 18 and 20 are positioned opposite each other within housing 16 and are removably coupled to housing 16. In one embodiment, electrodes 18 and 20 are made from a conductive metal in order to transmit an electrical discharge. In the illustrated embodiment of FIG. 1, electrode 18 is coupled to wire 22 and electrode 20 is coupled to wire 24, such that electrodes 18 and 20 are positioned at the ends of wires 22 and 24, respectively. In this embodiment, wires 22 and 24 are conductive and also coupled to electrical circuit 34 (e.g., electrical discharge circuit). In one embodiment, device 10 (or another similar device described herein) may include a plurality of electrodes coupled to electrical circuit 34 by flexible conductors (e.g., wires 22 and 24).

When device 10 is actuated, electrodes 18 and 20 are expelled or projected out from housing 16 (as shown in FIG. 1B) in order to attach to the target. As shown in FIG. 1C, device 10 may include cartridge 26, which provides a force to expel or project electrodes 18 and 20 from housing 16. In this embodiment, cartridge 26 is a compressed gas cartridge and is broken or punctured when device 10 is actuated (e.g., when trigger 14 is pulled or pressed), releasing pressurized gas into an area of housing 16 behind electrodes 18 and 20. The compressed gas expands when released from cartridge 26, building a pressure behind electrodes 18 and 20 to create a force sufficient to launch or project electrodes 18 and 20 out from housing 16 and through the air. When electrodes 18 and 20 are projected from housing 16, wires 22 and 24 remain connected or coupled to electrical circuit 34 and to electrodes 18 and 20, trailing behind electrodes 18 and 20, respectively, in order to maintain an electrical connection between electrodes 18 and 20 and electrical circuit 34. Electrodes 18 and 20 are configured to attach to the target in order to administer an electrical discharge to the target. In one embodiment, electrodes 18 and 20 include pointed or needled ends for piercing or penetrating clothing of the target in order to administer the discharge. In some embodiments, the penetration induced by the pointed or needled ends serve to adequately attach electrodes 18 and 20 to the target. However, electrodes 18 and 20 may also include additional attachment features for adhering or attaching electrodes 18 and 20 to the target. For instance, in the illustrated embodiment of FIGS. 1A-2, electrodes 18 and 20 include barbs 38 for attaching electrodes 18 and 20 to the target. Barbs 38 may include pointed ends configured to "grab" or attach to the target's clothing. Electrodes 18 and 20 may also include an adhesive material or substance, or any other attachment feature or component for attaching electrodes 18 and 20 to the target in order to deliver the electrical discharge to the target.

When electrodes 18 and 20 are attached or adhered to the biological target, an electric current may be sent or transmitted from circuit 34 through wires 22 and 24 and an electrical discharge may be delivered to the target by electrodes 18 and 20. In one embodiment, trigger 14 must be held in the actuated position in order to deliver the electrical discharge. In another embodiment, a predetermined electrical discharge is automatically delivered when electrodes 18 and 20 attach to the target. In another embodiment, electrodes 18 and 20 are projected from device 10 the first time trigger 14 is pressed or pulled (i.e., device 10 is actuated), and the electrical discharge is delivered when trigger 14 is pressed or pulled a second time. In one embodiment, a single electrical discharge is delivered by device 10, such as when trigger 14 is pressed or pulled (depending on the configuration of device 10). In another embodiment, device 10 delivers a series of electrical discharges (i.e., pulses) when device 10 is actuated or when trigger 14 is pressed or pulled to deliver the discharge.

In the illustrated embodiment, electrical circuit 34 receives electricity from batteries 36 to produce or generate a high-voltage, low-amperage electrical discharge that is administered by electrodes 18 and 20. Batteries 36 are housed within battery compartment 32 located within handle 12 in this embodiment, but may be otherwise positioned in other embodiments in order to deliver electricity to circuit 34. In one embodiment, circuit 34 includes transformers for boosting the voltage and reducing the amperage of the electrical discharge. Circuit 34 may also include an oscillator for fluctuating the electrical discharge to produce a specific pulse pattern of electricity (e.g., to generate a pulse frequency that mimics the body's own electrical signals). Circuit 34 may also include a capacitor for releasing the electrical discharge to electrodes 18 and 20. In one embodiment, an electrical discharge is "built up" (i.e., produced or generated) within the capacitor, and the electrical discharge is released to electrodes 18 and 20 through wires 22 and 24, respectively. Device 10 may also include electrode 28 and electrode 30 electrically connected to circuit 34 for delivering the electrical discharge. In the illustrated embodiment of FIGS. 1A-2, electrodes 28 and 30 are stationary or permanently connected to housing 16 of device 10 in order to administer the electrical discharge by direct contact with the target.

The electrical discharge delivered by device 10 may be intended to cause temporary neuromuscular incapacitation by interrupting the ability of the brain to control muscles in the body. In one embodiment, the electrical discharge is administered for a length of time at the discretion of the user (e.g., based on the user depressing a trigger). In another embodiment, the electrical discharge is automatically stopped after a relatively short period of time (e.g., an amount of time sufficient to incapacitate the target), even if a user of device 10 continues to hold trigger 14 in an actuated position. In one embodiment, device 10 delivers an electric discharge with a pulse frequency that mimics the target's own electrical signals, directing the target's muscles to move rapidly in a relatively short period of time, depleting the target's energy reserves and leaving the target temporarily incapacitated.

In one embodiment, electrodes 18 and 20 are used to monitor one or more physiological conditions (e.g., physiological indicators) of the target, which may include the target's involuntary physiological response(s) to the electrical discharge (e.g., involuntary muscular responses). In this embodiment, electrodes 18 and 20 attach to the target in order to measure or otherwise monitor physiological conditions of the target. Electrodes 18 and 20 may be configured to monitor the physiological conditions before, during, and/or after the electrical discharge is delivered to the target. In one embodiment, electrodes 18 and 20 generate one or more signals representing the monitored physiological conditions of the target and send the signals to a controller (e.g., controller 90) for use in controlling device 10.

Device 10 may also include sensor assembly 40 (e.g., sensors, detectors, monitors, etc.), which may also be used to monitor one or more physiological conditions (e.g., a second physiological condition or indicator) of the target. In the illustrated embodiment of FIGS. 1A-2, sensor assembly 40 is coupled to electrodes 18 and 20 such that sensor assembly 40 is launched or projected from housing 16 with electrodes 18 and 20 in order to attach to the target. In other embodiments, sensor assembly 40 may be otherwise positioned within device 10 or coupled to another component of device 10 in order to monitor the target, as may be suitable for the particular application of device 10. Sensor assembly 40 may be configured to monitor the physiological conditions before, during, and/or after an electrical discharge is delivered to the target. In one embodiment, sensor assembly 40 generates one or more signals (e.g., a second signal) representing the monitored physiological conditions of the target. Electrodes 18 and 20 and sensor assembly 40 may monitor the same physiological conditions of the target, or may be used to monitor separate and discrete physiological conditions, for example, based on the location or other characteristics of electrodes 18 and 20 and sensor assembly 40.

In some embodiments, the device sensors (i.e., sensor assembly 40 and/or electrodes 18 and 20) are configured to send signals to a controller such as controller 90. The device sensors can send one or more signals to controller 90 representing the physiological conditions monitored by electrodes 18 and 20. The device sensors may be configured to automatically send the signals to controller 90 at regular intervals (e.g., time-based intervals), to automatically send the signals to controller 90 when an event occurs (e.g., when the electrical discharge is delivered, when a first electric pulse in a series of pulses is delivered, during a "listening period" within a series of pulses, etc.), and/or to automatically send the signals to controller 90 as the signals are generated. The device sensors may also be configured to send the signals in response to a manual request (e.g., from a user of device 10) in other embodiments. Controller 90 is configured to receive and/or store the signals from the device sensors. In one embodiment, controller 90 is programmed or otherwise configured to use or interpret the signals received from the device sensors to modulate the electrical discharge (e.g., a predefined electrical discharge). Controller 90 may modulate the electrical discharge produced and/or delivered by device 10, as may be suitable for the particular application or function of device 10.

In one embodiment, controller 90 automatically adjusts or modulates the electrical discharge based on the signals received from the device sensors, such as by increasing or decreasing the intensity or duration of the electrical discharge. For instance, if the signals from the device sensors indicate that the target may be harmed by a delivered or continued electrical discharge (e.g., signs of fibrillation are detected, the target is relatively small, etc.), controller 90 may automatically decrease the intensity, lower a pulse repetition frequency, or shorten the duration of the electrical discharge to reduce the likelihood of permanent harm to the target. On the other hand, if the signals from the device sensors indicate that the target may be a continued threat to the user even after an electrical discharge having a selected magnitude is delivered (e.g., purposeful movement is detected after a delivered electrical discharge, the target is relatively large, etc.), controller 90 may automatically increase the intensity, increase a pulse repetition frequency, or lengthen the duration of the electrical discharge to increase the likelihood of temporarily incapacitating the target. The electrical discharge generated and/or administered by device 10 may be otherwise modulated in order to produce other outcomes, as may be suitable for the particular application of device 10. If device 10 is configured to deliver a single electrical discharge when trigger 14 is pressed, controller 90 may modulate the electrical discharge as the discharge is delivered and/or modulate the next discharge generated and/or delivered by device 10, each in response to the signals received from the device sensors. If device 10 is configured to deliver a series of electrical discharges or pulses when actuated, controller 90 may modulate the electrical discharge as the electrical discharge is delivered or controller 90 may modulate a future electrical discharge. For instance, controller 90 may modulate a future electrical discharge during a "listening period" (i.e., a period of time in between pulses for detecting or monitoring physiological indicator(s) of the biological target) in response to signals received during the listening period.

In one embodiment, electrodes 18 and 20 are configured to detect or monitor electrical activity produced by muscles of the biological target by electromyography (EMG). In this embodiment, electrodes 18 and 20 attach to the target such that electrodes 18 and 20 are able to measure electrical activity of muscles in either an active or a passive mode. In the active mode, electrodes 18 and 20 send an electrical current to a muscle of the target at or near electrodes 18 and 20. The electrical current is intended to electrically activate the muscle, detecting or recording an electrical potential (e.g., action potential) in response to the electrical current and sending one or more signals to controller 90 representing the electrical potential. In the passive mode, electrical potentials of the muscles near electrodes 18 and 20 are already present in sufficient amplitude to be measured directly. Controller 90 may use the signals from electrodes 18 and 20 to determine an activation level or movement of the target's muscles, modulating the electrical discharge produced or administered by device 10 based on the activation level or movement of the target's muscles. For instance, if the activation level or movement of the target's muscles indicates that the target is a threat to the user (before or after an electrical discharge is administered), controller 90 may either automatically apply an initial electrical discharge or automatically increase the intensity (e.g., current, voltage, etc.) of a subsequent electrical discharge in order to temporarily incapacitate the target.

In one embodiment, electrodes 18 and 20 are configured to detect or monitor electrical activity of the biological target's heart by electrocardiography (ECG). In this embodiment, electrodes 18 and 20 attach to the target such that electrodes 18 and 20 are able to monitor and record one or more heart conditions (i.e., physiological conditions related to the heart) of the target, similar to an ECG monitor or device. When attached to the target, electrodes 18 and 20 may be used to monitor heart conditions such as heart rate, regularity of heartbeat, a heart waveform, the size and position of heart chambers (i.e., heart chamber size and heart chamber position), the presence of any damage to the heart, and/or any other heart conditions suitable for the particular application of device 10. In one embodiment, electrodes 18 and 20 are configured to generate one or more signals representing the heart conditions and send the signals (e.g., an electrocardiographic signal) to controller 90. In this embodiment, controller 90 is programmed to control device 10 based on the signals, such as to modulate the electrical discharge generated and/or delivered by device 10. For instance, controller 90 may be programmed to use or interpret the signals to detect arrhythmia (i.e., heart arrhythmia) or fibrillation (i.e., heart fibrillation) in the target, or signs of potential arrhythmia or fibrillation, stopping the delivery of the electrical discharge or reducing the intensity or duration of the electrical discharge as necessary to reduce the likelihood of arrhythmia or fibrillation in the target. Electrodes 18 and 20 may be used to monitor the heart conditions of the target before the electrical discharge is delivered in order to deliver an appropriate electrical discharge. Electrodes 18 and 20 may also be used to monitor the heart conditions of the target during and/or after the electrical discharge is delivered in order to modulate the current or future electrical discharge.

In some embodiments, such as the illustrated embodiment of FIGS. 1A-2, sensor assembly 40 is coupled to electrodes 18 and 20 and is projected from housing 16 with electrodes 18 and 20 when device 10 is actuated. In one such embodiment, sensor assembly 40 includes an accelerometer for monitoring an acceleration (e.g., a proper acceleration) of the biological target. In this embodiment, sensor assembly 40 (including the accelerometer) attaches to the biological target in order to monitor the proper acceleration of the target, sending one or more signals to controller 90 representing the monitored acceleration of the biological target. Controller 90 is configured to receive the signals from sensor assembly 40 to determine whether the biological target is a continued threat, such as when the signals indicate purposeful movement. If the signals indicate that the target is a continued threat or otherwise requires an additional electrical discharge, controller 90 may modulate the electrical discharge generated and/or delivered by device 10. For instance, controller 90 may automatically increase the intensity of duration of the electrical discharge, increase a pulse repetition frequency, initiate the delivery of the electrical discharge, or otherwise activate or modulate device 10 in order to temporarily incapacitate the target.

In one embodiment, the accelerometer uses a frequency response of the target's motion to determine whether the target is experiencing an involuntary muscular response to the electrical discharge delivered by electrodes 18 and 20. In this embodiment, controller 90 may modulate the electrical discharge based on the involuntary response of the target. In another embodiment, the accelerometer monitors a vibration or amplitude of movement of the target (e.g., the target's muscle) in response to the electrical discharge, sending one or more signals to controller 90 representing the amplitude. In this embodiment, controller 90 is programmed to modulate the electrical discharge based on the involuntary response of the target in order to achieve a desired outcome (e.g., to incapacitate the target). In other embodiments, the accelerometer may use other methods to identify various movements (e.g., muscle movements) of the target or a part of the target's body and send signals to controller 90 indicative of the movements. Controller 90 may increase the intensity or duration of the electrical discharge if the target is insufficiently subdued or incapacitated, and/or decrease the intensity or duration of the electrical discharge if the target is adequately subdued or incapacitated.

In embodiments, device 10 is configured to deliver a series of pulses, such that controller 90 is programmed to adjust the time intervals between the pulses based on the signals received from sensor assembly 40. For instance, controller 90 may be programmed to apply a number of pulses, then pause for a period of time to monitor the physiological indicators of the target until the target shows signs of recovery (e.g., the physiological indicators indicate that the target is no longer incapacitated). Controller 90 may be programmed to then apply one or more additional pulses to again temporarily incapacitate the target. Controller 90 may also be programmed to modulate or adjust the intensity, time spacing, or magnitude of the pulses in response to signals from sensor assembly 40, such as to incapacitate the target for a specified amount of time or to ensure the target does not suffer more permanent harm. Controller 90 may also automatically adjust the number of pulses based on the signals received from sensor assembly 40, or otherwise adjust the frequency, duration, and/or intensity of the pulses as may be suitable for the particular application of device 10.

Figure 3A:
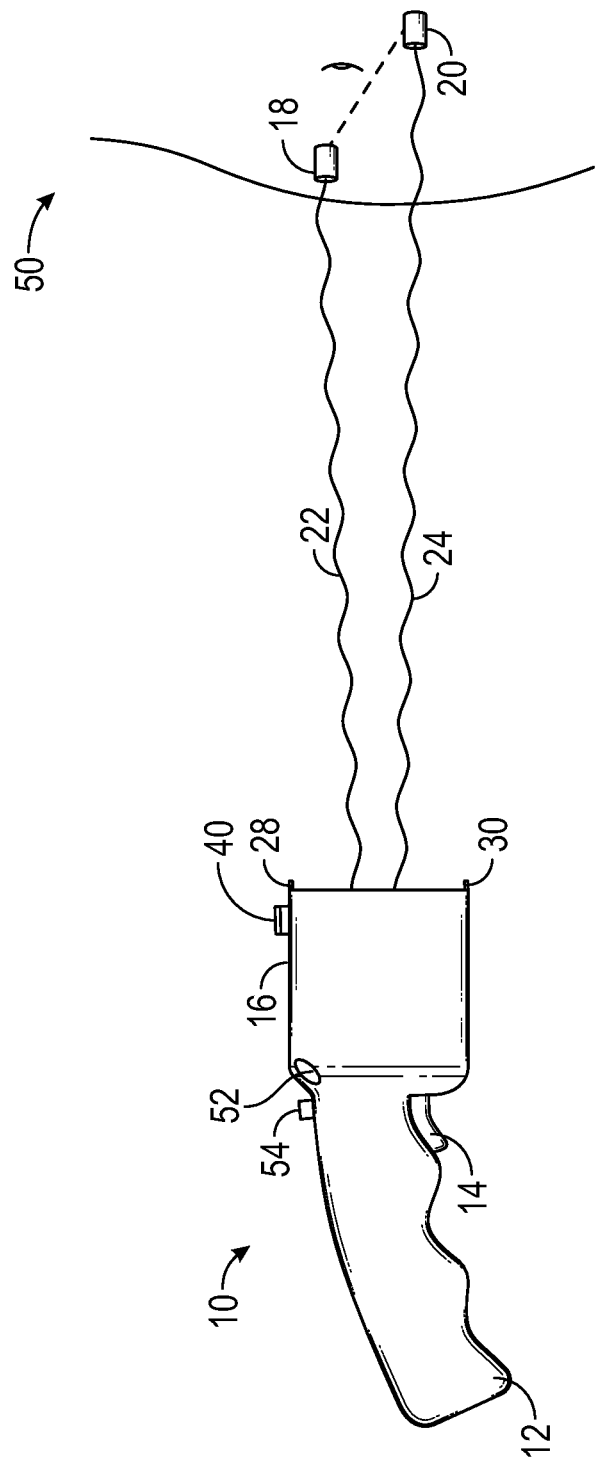
FIG. 3A is a schematic representation of an electroshock device attached to a target, according to one embodiment.

Referring now to FIG. 3, electrodes 18 and 20 are shown projected from device 10 and attached to biological target 50 (see FIG. 3A). In some embodiments, electrodes 18 and 20 are configured to measure a location or position of electrodes 18 and 20 once device 10 is actuated. For instance, electrodes 18 and 20 may send a signal to controller 90 for determining an absolute location or position of electrodes 18 and 20 on the body of target 50, or a location of electrodes 18 and 20 relative to each other. The electrical discharge delivered by device 10 may be modulated or otherwise controlled by controller 90 based on the separation or distance between electrodes 18 and 20 and/or the location of electrodes 18 and 20 on target 50. For example, if electrodes 18 and 20 are relatively close to one another, a smaller electrical discharge may be selected than if they are farther apart. Conversely, if electrodes 18 and 20 are very close to one another, a larger discharge may be selected based on the smaller target volume subjected to the discharge. The location of the current path between electrodes 18 and 20 may be used by controller 90 to determine the electrical discharge (e.g., a current path transiting a target's chest or leg may be more effective than one only transiting a right-handed target's left arm). In one embodiment, the electrical discharge is automatically modulated by controller 90 based on a proximity of electrodes 18 and 20 to the heart of target 50. In another embodiment, the electrical discharge is automatically modulated by controller 90 based on a proximity of the current path (e.g., a path of the electrical discharge as delivered by electrodes 18 and 20) to the heart of target 50. For instance, proximity of electrodes 18 and 20 or the current path to the heart may result in controller 90 selecting a smaller electrical discharge, so as to avoid harming the target's heart. In another embodiment, the electrical discharge is automatically modulated by controller 90 based on a location of electrodes 18 and 20 on the body of target 50, such as whether electrodes 18 and 20 are attached to a limb or the torso of target 50, or whether electrodes 18 and 20 are in the same or different limbs of target 50. The separation or distance between electrodes 18 and 20 and/or any of the above locations of electrodes 18 and 20 on target 50 may be automatically determined (e.g., by controller 90) based on the signals received from electrodes 18 and 20 and/or sensor assembly 40, or otherwise entered or inputted into device 10 such that controller 90 is able to automatically modulate the electrical discharge based on these conditions.

In some embodiments, electrodes 18 and 20 are configured to emit (i.e., send) and/or receive locating waves (e.g., ultrasound wave, sound wave, radio wave, etc.) in order to determine a location (e.g., a relative location, an absolute or actual location, etc.) of electrodes 18 and 20. For instance, electrodes 18 and 20 may send a signal related to the waves to controller 90 and controller 90 may determine a location of electrodes 18 and 20 based on the signal. Electrodes 18 and 20 may emit and/or receive locating waves automatically when device 10 is actuated, or electrodes 18 and 20 may emit and/or receive waves manually in response to a request or command from a user of device 10 (e.g., upon pressing a button or other actuator). In one embodiment, electrode 18 or 20 emits a wave that is received or reflected by the other electrode 18 or 20 in order to determine (e.g., by controller 90) a separation or distance between electrodes 18 and 20. In this embodiment, the separation or distance may be determined based on the time elapsed (i.e., a time delay) between when the wave is emitted by a first electrode and when the wave is received by a second electrode. In another embodiment, electrodes 18 and 20 emit one or more waves that are reflected by internal cavities or other parts of the body of target 50 (i.e., a body boundary) in order to determine or infer a location on the body of target 50 or to determine a location of the body boundary or internal cavity of target 50. In this embodiment, the location on the body or the location of the body boundary or internal cavity may be determined (e.g., by controller 90) based on the time elapsed between when the wave is emitted and when the wave is reflected, the strength of the reflected wave, or another characteristic or condition of the wave. For example, when electrode 18 is in a leg of the target, a wave emitted by it reflects off the side of the leg and the reflected wave is received by electrode 18 after a short time delay. Reflected waves are received by electrode 18 over a range of time delays, the shortest values due to reflections from the closest side of the leg, somewhat longer delays represent reflections from the opposite side of the leg, and then substantially longer delays represent reflections from waves traveling up or down the length of the leg. Controller 90 can analyze the spectrum of time delays (both the values and the relative strength of each return) to determine the position of electrode 18, determining that it is in a leg, as well as where in the leg it is located. Similar analysis can be done with electrode 20. Determination (by time delay measurements) of the separation between electrodes 18 and 20 can be used by controller 90 to determine, for example, that both are in the same leg, that one is in a leg and the other is in the target's torso, etc. The reflected wave can be received by the electrode that emitted the wave, or, alternatively, the reflected wave can be received by the other electrode. The waves (e.g., the reflected wave) may be used (e.g., by controller 90) to determine whether electrode 18 and/or 20 is attached to a limb or the torso of target 50. The waves may also be used to determine a closeness or proximity to boundaries of the torso or to internal cavities within target 50.

In one embodiment, electrode 18 emits a first locating wave and electrode 20 emits a second locating wave. The first locating wave and the second locating wave may be coherent with each other, and each have a phase or relative phase (i.e., phase offset, phase difference). In one embodiment, the first locating wave has an adjustable first phase and the second locating wave has an adjustable second phase. The first and second phases may be adjusted such that controller 90 can determine the location of electrodes 18 and 20 on target 50. The first phase and the second phase may be substantially different from each other (i.e., out of phase, having a phase difference) or the first phase and the second phase may be substantially similar to each other (i.e., in phase). In one embodiment, electrodes 18 and 20 are configured to emit coherently phased waves (i.e., waves having a constant relative phase or displaying a well-defined or constant phase relationship) intended to achieve a limited directionality of the waves (e.g., such that the waves interfere in defined directions). Each electrode may be configured to emit a wave in the direction of the opposite electrode in order to determine the separation or distance between electrodes 18 and 20, or to determine a position or location of electrode 18 or 20 on the body of target 50. Electrodes 18 and 20 may be configured to emit the waves at a selected beam angle (e.g., such that the waves interfere for a selected beam angle). In one embodiment, the beam angle of the waves (i.e., the direction the waves are emitted) may be varied or adjusted by adjusting the phase of the waves. In another embodiment, electrodes 18 and 20 are configured to use a phased reception (i.e., reception of the emitted or reflected waves) so that a direction of incoming emitted or reflected waves may be determined (e.g., by electrodes 18 and 20, by controller 90, etc.). In one embodiment, electrodes 18 and 20 determine a direction of waves reflected from body parts or internal cavities of target 50 so that a location or position of electrode 18 or 20 on target 50 may be determined (e.g., by controller 90).

In one embodiment, electrodes 18 and 20 emit the waves before the electrical discharge is generated and/or administered (e.g., delivered), sending one or more signals to controller 90 based on the reflection and/or reception of the waves such that controller 90 modulates the electrical discharge based on the signals before the discharge is delivered. In another embodiment, electrodes 18 and 20 emit the waves between a series of delivered electrical discharges (e.g., pulses), sending one or more signals to controller 90 such that controller 90 modulates the next electrical discharge to be delivered based on the signals. In this embodiment, controller 90 and/or device 10 may be programmed or otherwise configured to deliver one or more electrical discharges having a relatively low intensity (e.g., current level, voltage, etc.), and increase the intensity of the subsequent electrical discharge(s) if the signals indicate that the intensity should be increased in order to temporarily incapacitate target 50, or for another purpose according to the particular application of device 10. Similarly, controller 90 and/or device 10 may be programmed or otherwise configured to decrease the intensity of the subsequent electrical discharge(s) if the signals indicate that a higher intensity discharge is unnecessary (e.g., target 50 is temporarily incapacitated).

Still referring to FIG. 3, in some embodiments electrodes 18 and 20 are used to monitor the heartbeat of target 50 in order to determine a relative location of electrodes 18 and 20 on target 50 (e.g., for controller 90 to determine a relative location of electrodes 18 and 20 based on a signal from electrodes 18 and 20). In one such embodiment, electrodes 18 and 20 are configured to monitor (e.g., passively measure) a heartbeat reception (i.e., strength of the monitored heartbeat) at each electrode 18 and 20. Electrode 18 monitors a first heartbeat reception and electrode 20 monitors a second heartbeat reception. In this embodiment, electrodes 18 and 20 send signals to controller 90 representing the heartbeat reception at each of electrodes 18 and 20. Controller 90 is programmed to calculate a heartbeat reception differential (i.e., a difference between the heartbeat reception at electrode 18 and at electrode 20) in order to determine a relative distance of each electrode 18 and 20 from the heart of target 50 and/or a distance or separation between electrodes 18 and 20. Electrodes 18 and 20 may be configured to passively monitor the heartbeat (i.e., monitor the heartbeat absent an excitation or stimulus, such as delivery of the electrical discharge) in this embodiment, and may also send signals to controller 90 representing the heartbeat of target 50. In these embodiments, controller 90 may be programmed to determine a heartbeat reception differential from the signals, and thus determine a relative distance of each electrode 18 and 20 from the heart of target 50 and/or a distance or separation between electrodes 18 and 20. Electrodes 18 and 20 may use EMG or ECG in order to monitor one or more heart conditions of target 50, including the heartbeat.

In one embodiment, device 10 also includes optical sensors (e.g., cameras) for determining the relative location of electrodes 18 and 20 on a biological target (e.g., target 50). The optical sensors may be coupled to device 10 as part of sensor assembly 40, coupled individually to a component of device 10 (e.g., electrodes 18 and/or 20), or otherwise positioned on device 10. The optical sensors are configured to capture one or more images of electrodes 18 and 20 and/or target 50 and send one or more signals to controller 90 such that controller 90 can determine the relative location of electrodes 18 and 20 on target 50. In one embodiment, the optical sensors are configured to capture a first image of electrode 18 and a second image of electrode 20. In the illustrated embodiment of FIG. 3, the optical sensors are included as part of sensor assembly 40 and coupled to housing 16. In this embodiment, the optical sensors are oriented to face target 50 when device 10 is actuated, such that the optical sensors are likely to capture images of electrodes 18 and 20 when attached to target 50. In this embodiment, electrodes 18 and 20 may include identifying markings (e.g., a readable barcode, identifying paint marks, flags, LEDs, etc.) that enable the optical sensors to "pick up" or identify electrodes 18 and 20 on target 50. The optical sensors can detect the relative locations of electrodes 18 and 20, along with a distance or separation between electrodes 18 and 20 or a location on target 50. The optical sensors and/or sensor assembly 40 sends one or more signals to controller 90 regarding a location or separation of electrodes 18 and 20. Controller 90 may then modulate the electrical discharge delivered by device 10 based on signals from electrodes 18 and 20. In other embodiments, such as the illustrated embodiment of FIGS. 1A-2, the optical sensors may be included as part of sensor assembly 40 and coupled to electrodes 18 and 20. For instance, a first optical sensor may be coupled to electrode 18 and a second optical sensor may be coupled to electrode 20. In the illustrated embodiment of FIGS. 1A-2, the optical sensors capture images of target 50 as electrodes 18 and 20 approach target 50 (i.e., when device 10 is actuated). In this embodiment, the optical sensors and/or sensor assembly 40 send signals to controller 90 based on the captured images and controller 90 can modulate the electrical discharge delivered based on the signals.

In some embodiments, device 10 includes a defibrillation mode, such that device 10 includes or may be used as a defibrillator to treat a biological target exhibiting signs (i.e., physiological conditions) of fibrillation or a heart condition such as arrhythmia. In one such embodiment, controller 90 receives signals from electrodes 18 and 20 and/or sensor assembly 40 and determines whether defibrillation is necessary or desirable based on the signals. Device 10 can be automatically or manually converted to the defibrillation mode in order to deliver one or more defibrillation pulses (i.e., electrical discharges) to the target (e.g., target 50). In one embodiment, device 10 includes indicator 52 (e.g., positioned on handle 12, coupled to controller 90) for providing an indication to a user of electroshock device 10 that fibrillation is detected. In some embodiments, electrical circuit 34 is configured to generate an electrical discharge (i.e., defibrillation pulses) capable of re-establishing a target's "normal" heart rhythm (i.e., capable of delivering the necessary electrical energy to the heart to establish a stable heartbeat). For instance, electrical circuit 34 may include a capacitor capable of storing the electrical energy necessary to defibrillate the heart of the target (i.e., to generate an electrical discharge capable of defibrillating the heart). Device 10 may also include a switchgear (e.g., pulse-tailoring switchgear) to deliver an electrical discharge from electrical circuit 34 in a defibrillation pulse form (i.e., having the intensity and frequency necessary to defibrillate the heart of the target). The switchgear may be coupled to electrical circuit 34 or otherwise positioned within device 10 in order to enable one or more defibrillating pulses to be delivered by device 10. In another embodiment, device 10 includes a defibrillating pulse generation circuit similar to electrical circuit 34. In this embodiment, the defibrillating pulse generation circuit is configured to produce or generate the defibrillating pulse and device 10 is configured to deliver the defibrillating pulse to a target via electrodes 18 and 20 or separate defibrillating leads.

In one embodiment, electrodes 18 and 20 are used as leads for delivering the defibrillation pulses to the target, having a defibrillating mode and an electroshock mode. In this embodiment, electrodes 18 and 20 are expelled from housing 16 when device 10 is actuated, attaching to target 50 as shown in FIG. 3A. Once attached, electrodes 18 and 20 and/or sensor assembly 40 may be used to monitor physiological conditions of target 50, sending signals to controller 90 representing the physiological conditions in order to determine if defibrillation is necessary. Controller 90 may be programmed to determine if defibrillation is necessary before and/or after the incapacitating electrical discharge (i.e., an electrical discharge intended to temporarily incapacitate target 50) is delivered to target 50. If the physiological conditions indicate that defibrillation is necessary or desirable (as calculated or determined by controller 90), defibrillation pulses may be delivered to target 50 by electrodes 18 and 20.

Figure 3B:
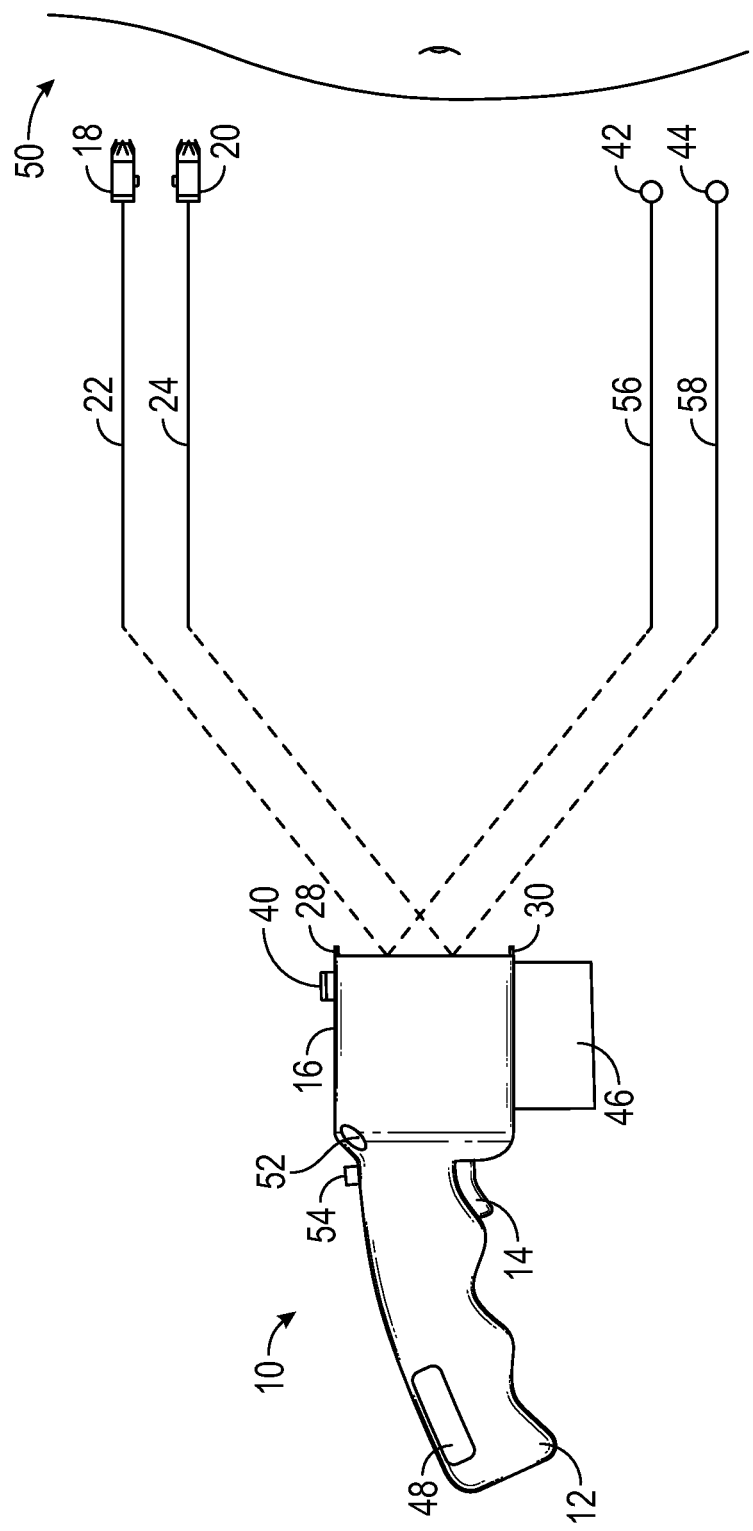
FIG. 3B is an illustration of an electroshock device having separate defibrillation leads, according to one embodiment.

Referring to FIG. 3B, in other embodiments, device 10 includes separate defibrillation leads 42 and 44 (e.g., electrodes, defibrillating electrodes, etc.) for delivering the defibrillation pulse(s). Lead 42 and lead 44 can be stored in storage compartment 46 coupled to device 10. Alternatively, leads 42 and 44 can be stored in storage compartment 48 integrated into device 10 (e.g., within handle portion 12, etc.). In one embodiment, lead 42 is coupled to wire 56 and lead 44 is coupled to wire 58, such that leads 42 and 44 are positioned at the ends of wires 56 and 58, respectively. In this embodiment, wires 56 and 58 are conductive. Wires 56 and 58 may be coupled to electrical circuit 34 in order to deliver the defibrillation pulses to leads 42 and 44, respectively. When leads 42 and 44 are projected (e.g., expelled, ejected, launched, etc.) from device 10, wires 56 and 58 remain attached to device 10 so that leads 42 and 44 remain coupled to device 10. In some embodiments, leads 42 and 44 are configured to be manually positioned on a target by a user of device 10. Leads 42 and 44 can be similar to electrodes 18 and 20. Thus, the description herein of electrodes 18 and 20 applies similarly to the defibrillation leads, and description of the delivery of the defibrillation pulse(s) as described below in reference to electrodes 18 and 20 applies similarly to embodiments of device 10 having the separate defibrillation leads.

In some embodiments, device 10 automatically delivers the defibrillation pulses to target 50 when controller 90 determines defibrillation is necessary. In one such embodiment, controller 90 calculates or determines the location or position of electrodes 18 and 20 on target 50 based on the signals from electrodes 18 and 20 and/or sensor assembly 40 in order to determine if electrodes 18 and 20 are in a location suitable for delivering defibrillation pulses. If the electrodes are suitably positioned, device 10 may automatically deliver the defibrillation pulses to target 50 through electrodes 18 and 20; controller 90 may select characteristics of the defibrillation pulses based on the locations of electrodes 18 and 20. If not, device 10 may provide a signal (e.g., a sound, a light or light pattern, a vibration, etc.) to the user indicating that electrodes 18 and/or 20 must be repositioned on target 50 in order to effectively provide defibrillation. Once electrodes 18 and 20 are properly positioned (e.g., by the user of device 10), the user of device 10 is able to deliver the defibrillating pulse(s) to target 50, such as by actuating trigger 14 (e.g., defibrillating trigger, defibrillation actuator). When trigger 14 is actuated, a defibrillation signal may be sent to electrical circuit 34 and/or controller 90 in order to deliver a defibrillating pulse to target 50. In other embodiments, device 10 is configured to deliver the defibrillation pulses only in response to (manual) manipulation by the user. In one such embodiment, device 10 provides a signal (e.g., a sound, a light or light pattern, a vibration, etc.) to the user indicating that defibrillation necessary. The signal may be provided by indicator 52. The user is able to manipulate device 10 (e.g., press a button, flip a switch, etc.) to deliver the defibrillation pulse(s) as needed. Device 10 may also include separate defibrillation actuator 54 coupled to controller 90 and having an actuated position for sending a defibrillation signal to controller 90 to deliver the defibrillating pulse. Defibrillation actuator 54 is shown coupled to a top portion of handle 12 in FIG. 3, but defibrillation actuator 54 may be otherwise positioned on device 10 in other embodiments. The user may press or otherwise actuate defibrillation actuator 54 to deliver the defibrillating pulse. As noted above, device 10 may also be configured to provide a signal to the user indicating that electrodes 18 and 20 are not properly placed. Device 10 may then prevent delivery of the defibrillating pulse(s) until electrodes 18 and 20 are properly placed on target 50. Device 10 may include a switch or button for converting device 10 to defibrillation mode and/or for delivering the defibrillation pulse(s).

Figure 4:
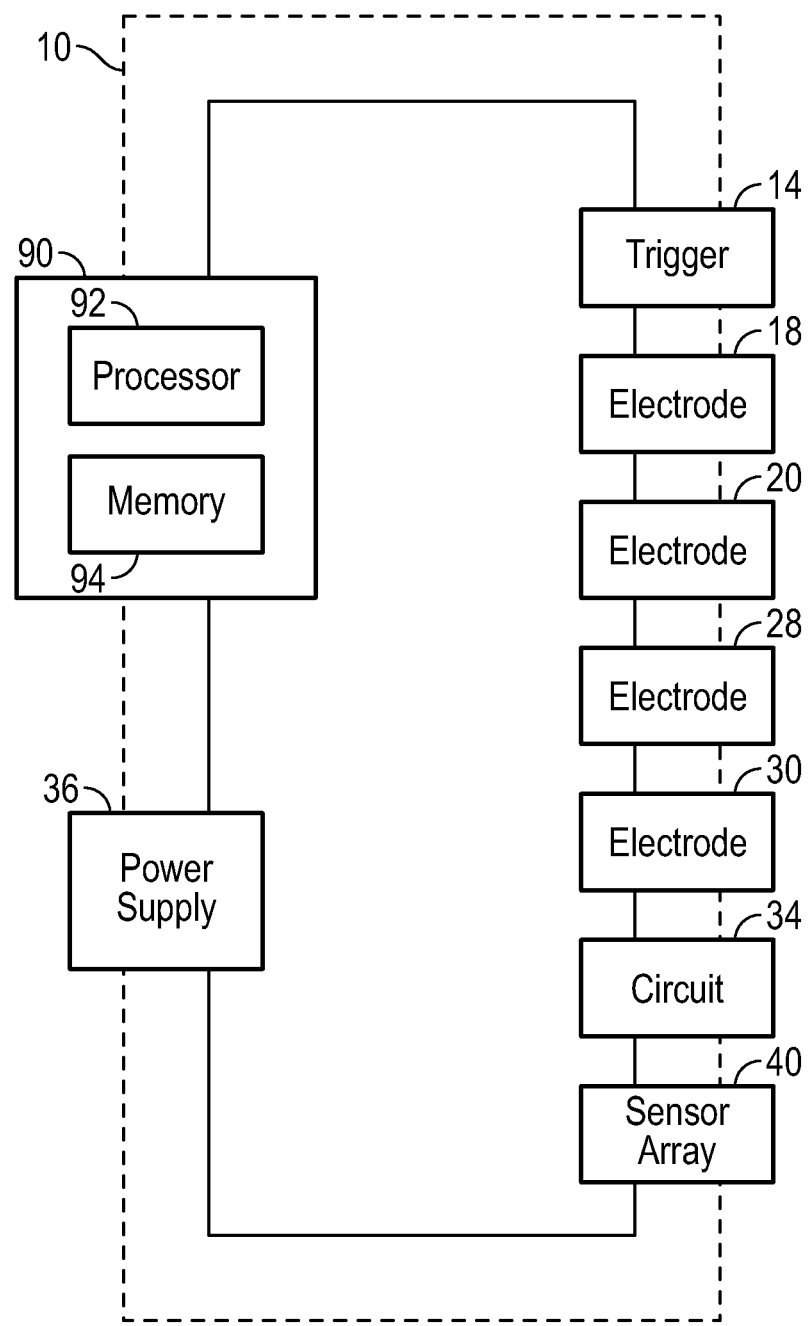
FIG. 4 is a block diagram of a controller for an electroshock device, according to one embodiment.

Referring now to FIG. 4, a block diagram of controller 90 is shown according to one embodiment. Controller 90 may be used to control one or more components of device 10 (e.g., electrical circuit 34, electrodes 18 and 20, etc.), as well as to perform any calculations, functions or processes of device 10 described above. In the illustrated embodiment of FIG. 4, controller 90 is shown as a component of device 10, and may be used to control the operation of one or more components of device 10. However, in other embodiments, controller 90 may be an independent component, and be configured to wirelessly control device 10.

In one embodiment, controller 90 includes processor 92 and a memory device shown as memory 94. Memory 94 stores programming instructions that, when executed by processor 92, control the operations of device 10, including the production and delivery of an electrical discharge through electrodes 18 and 20. In one embodiment, processor 92 is included as part of a processing circuit also including memory 94. Processor 92 may be implemented as a general-purpose processor, an application specific integrated circuit (ASIC), one or more field programmable gate arrays (FPGAs), a digital-signal-processor (DSP), a group of processing components, or other suitable electronic processing components. Memory 94 is one or more devices (e.g., RAM, ROM, Flash Memory, hard disk storage, etc.) for storing data and/or computer code for facilitating the various processes described herein. Memory 94 may be or include non-transient volatile memory or non-volatile memory. Memory 94 may include database components, object code components, script components, or any other type of information structure for supporting the various activities and information structures described herein. Memory 94 may be communicably connected to processor 92 and provide computer code or instructions to processor 92 for executing the processes described herein.

Controller 90 is in electrical communication with various components of device 10, including trigger 14, electrodes 18, 20, 28, and 30, electrical circuit 34, and sensor assembly 40. In one embodiment, controller 90 is electrically connected to each of these components of device 10 by a physical wire (e.g., wires 22 and 24). In other embodiments, controller 90 may be connected to one or more of the components of device 10 by a remote (e.g., wireless) connection, as may be suitable for the particular application of controller 90 and/or device 10.

In one embodiment, controller 90 is programmed to command electrical circuit 34 to generate the electrical discharge, to produce a defibrillating pulse, to modulate the intensity or duration of the electrical discharge, to control a multi-phase electrical discharge sequence, or to command electrical circuit 34 or any other connected components to perform any functions described above related to device 10, based on the signals received from sensor assembly 40 and/or electrodes 18 and 20 indicating the one or more physiological conditions of the target. In one embodiment, controller 90 is programmed to store or record any signals or commands sent or received, or any other information related to device 10 within memory 94 to be available for upload. The stored information may be uploaded from memory 94 upon request, or by a schedule.

Controller 90 receives operational electrical power from a power supply (e.g., batteries 36). In one embodiment, the power supply provides power to controller 90 and all components of device 10, including circuit 34. The power supply may be any suitable power source, including, but not limited to, battery 36, a solar power source, grid power, or a combination thereof. In arrangements where the power supply includes a rechargeable battery, the battery may be charged during operation through another power source (e.g., a solar panel, etc.).

Figure 5:
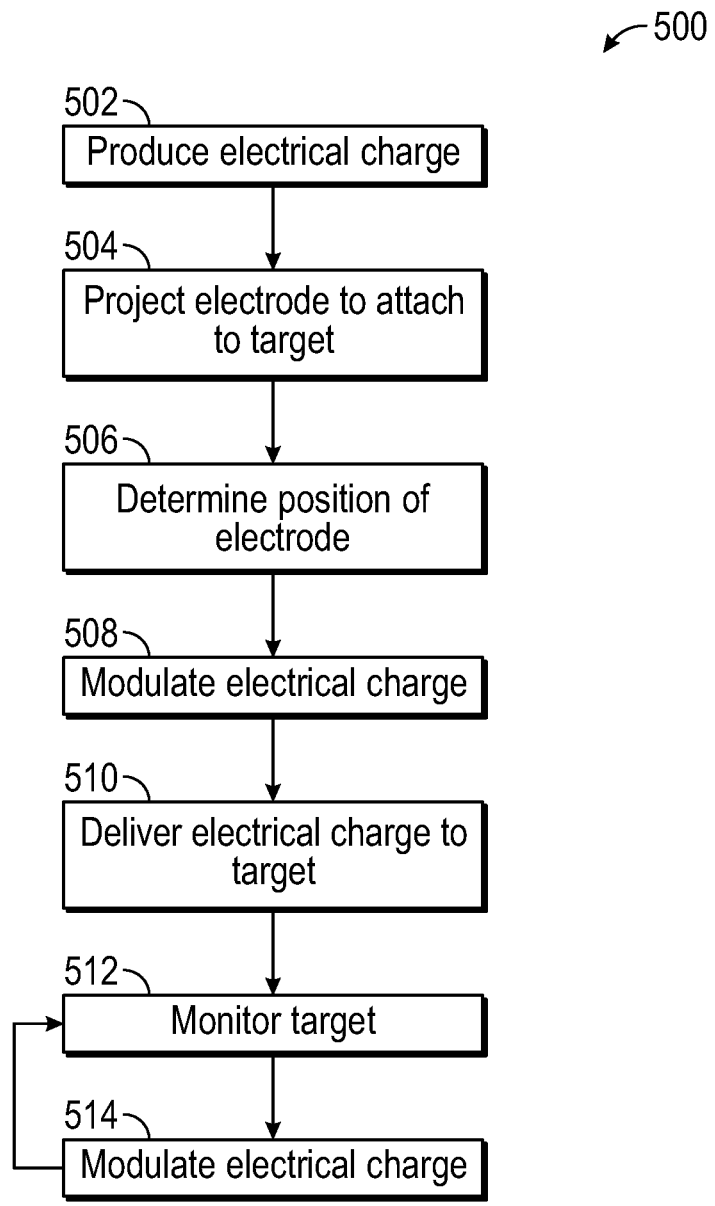
FIG. 5 is a flow chart representation of a method for measuring a physiological response of a target to an electrical discharge and modulating the electrical discharge based on the response, according to one embodiment.

Referring now to FIG. 5, flow chart 500 shows a method for delivering an electrical discharge to a target (e.g., target 50), according to one embodiment. The method may be executed by device 10, including controller 90. An electrical discharge is generated at 502. The electrical discharge may be generated by electrical circuit 34 of device 10. At 504, an electrode (e.g., electrode 18, electrode 20, etc.) is attached to the target by projecting the electrode from an electroshock device (e.g., device 10). At 506, a position of the electrode is determined, such as described above (e.g., by sending and receiving locating waves while attached to the target). At 508, the electrical discharge is modulated based at least in part on the position of the electrode. For instance, the intensity (e.g., voltage or current, duration, etc.) of the electrical discharge may be decreased if the electrode is at or near the heart. On the other hand, the intensity of the electrical discharge may be increased if the electrode is attached to a limb. The electrical discharge may be modulated automatically based on the position of the electrode or manually (e.g., by a user in response to a signal from device 10). At 510, the electrical discharge is delivered to the target via the electrode. At 512, a physiological condition of the target is monitored, which may include monitoring one or more heart conditions or any other physiological conditions described above. At 514, the electrical discharge is modulated based at least in part on the physiological condition. For instance, if the target has been sufficiently subdued, the intensity of the electrical discharge may be decreased or the electrical discharge may be stopped or prevented. In other embodiments, the method may include any of the steps shown in FIG. 5 in any combination, and may also include any additional steps as described above.

Figure 6:
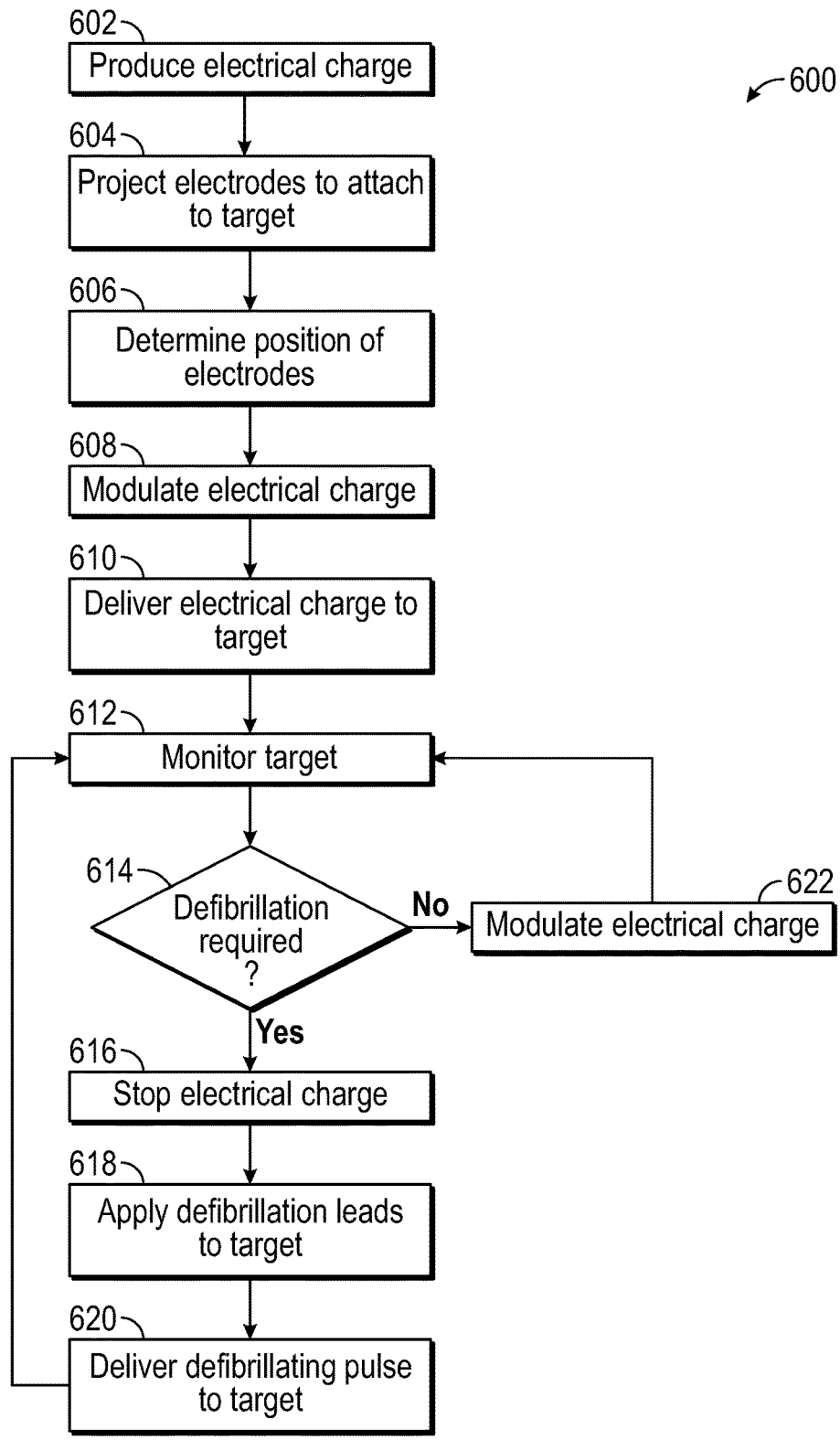
FIG. 6 is a flow chart representation of a method for measuring a physiological response of a target to an electrical discharge and delivering a defibrillating pulse based on the response, according to one embodiment.

Referring now to FIG. 6, flow chart 600 shows a method for delivering a defibrillating pulse to a target (e.g., target 50), according to one embodiment. The method may be executed by device 10, including controller 90. An electrical discharge is generated at 602, an electrode is attached to the target by projecting the electrode from a device (e.g., device 10) at 604, a position of the electrode on the target is determined at 606, the electrical discharge is modulated based at least in part on the position of the electrode at 608, the electrical discharge is delivered to the target at 610, one or more physiological conditions of the target are monitored at 612. At 614, it is determined whether defibrillation is required based at least in part on the physiological conditions of the target. This step may include determining whether heart fibrillation is present within the target, or whether one or more physiological conditions suggest an imminent heart fibrillation. If defibrillation is required, delivery of the electrical discharge may be stopped at 616 and defibrillation leads (e.g., electrodes 18 and 20, defibrillation leads 42 and 44, etc.) are applied to the target at 618. At 620, a defibrillating pulse is delivered to the target via the defibrillation leads. If defibrillation is not required, the electrical discharge is modulated at 622 and the target is again monitored at 612. In other embodiments, the method may include any of the steps shown in FIG. 6 in any combination, and may also include any additional steps as described above.

The construction and arrangement of the apparatus, systems and methods as shown in the various embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials, colors, orientations, etc.). For example, some elements shown as integrally formed may be constructed from multiple parts or elements, the position of elements may be reversed or otherwise varied and the nature or number of discrete elements or positions may be altered or varied. Accordingly, all such modifications are intended to be included within the scope of the present disclosure. The order or sequence of any process or method steps may be varied or re-sequenced according to alternative embodiments. Other substitutions, modifications, changes, and omissions may be made in the design, operating conditions and arrangement of the described embodiments without departing from the scope of the present disclosure.

The present disclosure contemplates methods, systems and program products on any machine-readable media for accomplishing various operations. The embodiments of the present disclosure may be implemented using existing computer processors, or by a special purpose computer processor for an appropriate system, incorporated for this or another purpose, or by a hardwired system. Embodiments within the scope of the present disclosure include program products comprising machine-readable media for carrying or having machine-executable instructions or data structures stored thereon. Such machine-readable media can be any available media that can be accessed by a general purpose or special purpose computer or other machine with a processor. By way of example, such machine-readable media can comprise RAM, ROM, EPROM, EEPROM, CD-ROM or other optical disk storage, magnetic disk storage or other magnetic storage devices, or any other medium which can be used to carry or store desired program code in the form of machine-executable instructions or data structures and which can be accessed by a general purpose or special purpose computer or other machine with a processor. When information is transferred or provided over a network or another communications connection (either hardwired, wireless, or a combination of hardwired or wireless) to a machine, the machine properly views the connection as a machine-readable medium. Thus, any such connection is properly termed a machine-readable medium. Combinations of the above are also included within the scope of machine-readable media. Machine-executable instructions include, for example, instructions and data which cause a general purpose computer, special purpose computer, or special purpose processing machines to perform a certain function or group of functions.

The terms "coupled," "connected," and the like as used herein mean the joining of two members directly or indirectly to one another. Such joining may be stationary (e.g., permanent) or moveable (e.g., removable or releasable). Such joining may be achieved with the two members or the two members and any additional intermediate members being integrally formed as a single unitary body with one another or with the two members or the two members and any additional intermediate members being attached to one another. Such joining may be communicative, rather than physical.

Although the figures may show or the description may provide a specific order of method steps, the order of the steps may differ from what is depicted. Also two or more steps may be performed concurrently or with partial concurrence. Such variation will depend on various factors, including software and hardware systems chosen and on designer choice. All such variations are within the scope of the disclosure. Likewise, software implementations could be accomplished with standard programming techniques with rule based logic and other logic to accomplish the various connection steps, processing steps, comparison steps and decision steps.

What is claimed is:

1. A method for delivering an electrical discharge to a target by an electroshock device, the method comprising:
   attaching one or more electrodes to the target by projecting the one or more electrodes from the electroshock device;
   delivering the electrical discharge to the target via the one or more electrodes;
   monitoring a physiological condition of the target using the one or more electrodes;
   determining a position of the one or more electrodes at the target; and
   modulating the electrical discharge based on the physiological condition and the position of the one or more electrodes.

2. The method of claim 1, wherein the physiological condition includes an involuntary muscular condition of the target, and wherein the electrical discharge is modulated based on the involuntary muscular condition.

3. The method of claim 2, wherein the involuntary muscular condition includes at least one of an activation level, movement, electrical activity, and electrical potential associated with a muscle of the target.

4. The method of claim 1, wherein the physiological condition includes an involuntary response to delivery of the electrical discharge, and wherein the electrical discharge is modulated based on the involuntary response.

5. The method of claim 1, further comprising:
   determining whether the target is sufficiently subdued based on the physiological condition; and
   modulating the electrical discharge based on the determination of whether the target is sufficiently subdued.

6. The method of claim 1, wherein the electrical discharge includes a series of pulses in which the initial pulse is predefined, and wherein any subsequent pulses are modulated based on the physiological condition of the target.

7. The method of claim 6, wherein the series of pulses are separated by one or more listening periods, and wherein modulating the electrical discharge includes modulating the subsequent pulses based on the physiological condition monitored during the one or more listening periods.

8. The method of claim 1, further comprising:
   based on the physiological condition, determining that the target will be harmed by the electrical discharge; and
   modulating at least one of an intensity and a duration of the electrical discharge based on the determination that the target will be harmed.

9. The method of claim 1, wherein the electrical discharge is modulated prior to delivering the electrical discharge to the target.

10. The method of claim 9, wherein the physiological condition of the target is automatically monitored upon attachment of the one or more electrodes to the target.

11. The method of claim 9, further comprising:
   preventing delivery of the electrical discharge prior to monitoring the physiological condition.

12. An electroshock device for delivering an electrical discharge to a target, the electroshock device comprising:
   an electrical discharge circuit configured to produce an electrical discharge;
   one or more electrodes coupled to the electrical discharge circuit and configured to:
      attach to the target by projecting from the electroshock device; and
      deliver the electrical discharge to the target; and
   a controller communicatively coupled to the electrical discharge circuit and the one or more electrodes, the controller configured to:
      monitor a physiological condition of the target based on information received from the one or more electrodes;
      determine whether the physiological condition indicates continued purposeful movement of the target based on the information; and
      modulate the electrical discharge based on the physiological condition and the determination.

13. The device of claim 12, wherein the physiological condition includes an involuntary muscular condition of the target, and wherein the controller modulates the electrical discharge based on the involuntary muscular condition.

14. The device of claim 13, wherein the involuntary muscular condition includes at least one of an activation level, movement, electrical activity, and electrical potential associated with a muscle of the target.

15. The device of claim 12, wherein the physiological condition includes an involuntary response to delivery of the electrical discharge, and wherein the controller modulates the electrical discharge based on the involuntary response.

16. The device of claim 12, wherein the controller is configured to:
   determine whether the target is sufficiently subdued based on the physiological condition; and
   modulate the electrical discharge based on the determination of whether the target is sufficiently subdued.

17. The device of claim 12, wherein the controller is configured to:
   determine a position of the one or more electrodes at the target; and
   modulate the electrical discharge based on the position of the one or more electrodes.

18. The device of claim 12, wherein the electrical discharge includes a series of pulses in which the initial pulse is predefined, and wherein the controller is configured to modulate any subsequent pulses based on the physiological condition of the target.

19. The device of claim 18, wherein the series of pulses are separated by one or more listening periods, and wherein the controller is configured to modulate the subsequent pulses based on the physiological condition monitored during the one or more listening periods.

20. The device of claim 12, wherein the controller is configured to:
   based on the physiological condition, determine that the target will be harmed by the electrical discharge; and
   modulate at least one of an intensity and a duration of the electrical discharge based on the determination that the target will be harmed.

21. The device of claim 12, wherein the electrical discharge is modulated prior to delivering the electrical discharge to the target.

22. The device of claim 21, wherein the controller is configured to automatically monitor the physiological condition of the target upon attachment of the one or more electrodes to the target.

23. The device of claim 21, wherein the controller is configured to prevent delivery of the electrical discharge prior to monitoring the physiological condition.

24. A method for delivering a defibrillating pulse to a target by an electroshock device, the method comprising:
   delivering an electrical discharge to the target via an electrode projected from the electroshock device;
   monitoring a physiological condition of the target;
   determining that the defibrillating pulse is required based on the physiological condition;
   delivering the defibrillating pulse to the target based on the determination; and
   modulating the defibrillating pulse based on determining whether the target is temporarily incapacitated.

25. The method of claim 24, wherein the electrode is one of a plurality of electrodes projected from the electroshock device.

26. The method of claim 24, further comprising discontinuing the electrical discharge based on a determination that the defibrillating pulse is required.

27. The method of claim 24, wherein determining whether the defibrillating pulse is required includes determining whether at least one of a heart arrhythmia or heart fibrillation is present in the target.

28. The method of claim 24, further comprising modulating at least one of the electrical discharge and the defibrillating pulse based on the physiological condition.

29. The method of claim 24, wherein the defibrillating pulse is delivered by applying defibrillation leads to the target.

30. The method of claim 24, wherein the defibrillating pulse is delivered by the electrode.

31. The method of claim 24, further comprising providing an indication that the defibrillating pulse is required.

32. The method of claim 31, wherein manual manipulation of the electroshock device is required to deliver the defibrillating pulse.

33. The method of claim 24, wherein the physiological condition is monitored by the electrode.

34. The method of claim 24, further comprising attaching the electrode to the target prior to delivering the electrical charge by projecting the electrode from an electroshock device.

* * * * *